(12) United States Patent
Tsuchino et al.

(10) Patent No.: US 6,370,229 B1
(45) Date of Patent: Apr. 9, 2002

(54) RADIATION IMAGE READING SYSTEM AND RADIATION IMAGE READING METHOD

(75) Inventors: Hisanori Tsuchino; Masayuki Nakazawa, both of Hino (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 09/484,569

(22) Filed: Jan. 18, 2000

(30) Foreign Application Priority Data

Jan. 21, 1999 (JP) .......................................... 11-013149

(51) Int. Cl.⁷ ................................................. H05G 1/26
(52) U.S. Cl. ........................ 378/165; 378/114; 378/115; 378/116; 378/162; 250/584; 600/508
(58) Field of Search ................................ 250/582, 584; 378/114, 115, 116, 162, 165; 600/508

(56) References Cited

U.S. PATENT DOCUMENTS 5,335,172 A * 8/1994 Matsumoto et al. ........ 250/582
6,004,276 A * 12/1999 Wright et al. ............... 600/508

* cited by examiner

Primary Examiner—Robert H. Kim
Assistant Examiner—Therese Barber
(74) Attorney, Agent, or Firm—Frishauf, Holtz, Goodman, Langer & Chick, P.C.

(57) ABSTRACT

A radiation image reading system, comprises a plurality of reading apparatus to read a radiation image and to produce image data; and an information transmitting apparatus to transmit information regarding a patient to at least a reading apparatus of the plurality of reading apparatus; wherein when the information regarding the patient transmitted by the information transmitting apparatus is canceled, the information regarding the patient is transmitted by the information transmitting apparatus to another reading apparatus other than the reading apparatus to which the information regarding the patient was firstly transmitted.

30 Claims, 2 Drawing Sheets

FIG. 2

| PATIENT NAME | ID No. | RADIOGRAPHING REGION | RADIOGRAPHING AND READING ROOM |
|---|---|---|---|
| TARO ○○ | 90111 | BREAST | A |
| ○○ YAMADA | 99123 | BREAST | B |
| HANAKO ○○ | 00789 | BREAST | A |
| ○○ SUZUKI | 00456 | BREAST | B |
| ICHIRO ○○ | 90531 | BREAST | C |
| ○○ SATO | 00157 | BREAST | A |

FIG. 3 (a)

| PATIENT NAME | ID No. | RADIOGRAPHING REGION | RADIOGRAPHING AND READING ROOM |
|---|---|---|---|
| TARO ○○ | 90111 | BREAST | A |
| HANAKO ○○ | 00789 | BREAST | A |
| ○○ SATO | 00157 | BREAST | A |

FIG. 3 (b)

| PATIENT NAME | ID No. | RADIOGRAPHING REGION | RADIOGRAPHING AND READING ROOM |
|---|---|---|---|
| ○○ YAMADA | 99123 | BREAST | B |
| ○○ SUZUKI | 00456 | BREAST | B |
| ○○ SATO | 00157 | BREAST | B |

RADIATION IMAGE READING SYSTEM AND RADIATION IMAGE READING METHOD

BACKGROUND OF THE INVENTION

The present invention relates to a radiation image reading system which reads a radiation image obtained by radiographing a patient for a diagnosis in a hospital, and to a radiation image reading method.

There have been known a radiation image radiographing apparatus which conducts irradiation of radiation on a specific region of a patient in a medical institution such as a hospital and accumulates and records image information on a semiconductor X-ray detecting element or on an accelerated phosphor (stimulable phosphor), and a radiation image reading apparatus for reading the aforesaid image information. In a general hospital having many patients, there are installed many radiation image radiographing apparatuses and many radiation image reading apparatuses, and patients are radiographed to obtain radiation images which are read immediately after radiographing.

When plural apparatuses are installed as stated above, radiographing of a patient for radiation images and reading of the radiation images which are to be conducted on each apparatus which once accepted the patient are sometimes canceled for various reasons such as maintenance or troubles of each apparatus, or availability of a radiologist, and radiographing and reading need to be conducted on another apparatus. In such a case, when an apparatus to conduct radiation image reading and radiographing can not be switched to another apparatus smoothly, confusion takes place easily in the hospital having a large number of patients, for example. If such confusion takes place frequently, there is a fear that a diagnosis by means of radiation images is affected adversely, which is not preferable.

SUMMARY OF THE INVENTION

An object of the invention is to provide a radiation image reading system wherein even when radiographing of a patient for radiation images and reading of the radiation images are canceled on each apparatus which accepted the patient, that apparatus can be switched to another apparatus for reading radiation images smoothly and simply, when plural radiation image reading apparatuses are installed, and to provide a radiation image reading method.

The above object can be attained by the following system and method.

A radiation image reading system, comprises:
a plurality of reading apparatus to read a radiation image and to produce image data; and
an information transmitting apparatus to transmit information regarding a patient to at least a reading apparatus of the plurality of reading apparatus; wherein when the information regarding the patient transmitted by the information transmitting apparatus is canceled, the information regarding the patient is transmitted by the information transmitting apparatus to another reading apparatus other than the reading apparatus to which the information regarding the patient was firstly transmitted.

A radiation image reading system, comprises:
a plurality of reading apparatus to read a radiation image of a patient,
at least one of the plurality of reading apparatus comprising a display to indicate information regarding the patient, wherein the display is capable of indicating information regarding a patient whose image is expected to be read by the other reading apparatus; and
the reading apparatus further comprising canceling means for canceling the information regarding the patient whose image is expected to be read by the other reading apparatus,
wherein when the canceling means of a reading apparatus cancels the information regarding the patient whose image is expected to be read by the other reading apparatus, the canceled information regarding the patient is transmitted from the other reading apparatus to the reading apparatus.

A radiation image reading system, comprises:
a plurality of reading apparatus to read a radiation image of a patient,
at least one of the plurality of reading apparatus comprising a display to indicate information regarding the patient, wherein the display is capable of indicating information regarding a patient whose image is expected to be read by the other reading apparatus; and
the reading apparatus further comprising canceling means for canceling the information regarding the patient whose image is expected to be read by itself,
wherein when the canceling means of a reading apparatus cancels the information regarding the patient whose image is expected to be read by the reading apparatus, the canceled information regarding the patient is transmitted from the reading apparatus to the other reading apparatus.

A radiation image reading system, comprises:
inputting means for inputting information regarding a patient;
a display to indicate the information regarding the patient inputted by the inputting means, the display capable of indicating information regarding a patient inputted to other reading apparatus;
canceling means for canceling the information regarding the patient inputted to the other reading apparatus; and
receiving means for receiving the information regarding the patient canceled by the canceling means from the other reading apparatus.

A radiation image reading system, comprises:
inputting means for inputting information regarding a patient;
a display to indicate the information regarding the patient inputted by the inputting means, the display capable of indicating information regarding a patient inputted to other reading apparatus; and
a controller to control so as to transmit the information regarding the patient to other reading apparatus when the information regarding the patient inputted by the inputting means is canceled by the other reading apparatus.

A method of reading a radiation image, comprises steps of:
inputting receiving information to reception inputting means provided at a position to receive a patient;
transmitting at least a radiation image reading apparatus of a plurality of radiation image reading apparatus;
canceling the information regarding the patient transmitted to the radiation image reading apparatus of the plurality of radiation image reading apparatus; and
transmitting the canceled information regarding the patient to another radiation image reading apparatus other than the radiation image reading apparatus to which the information regarding the patient was firstly transmitted.

Further, the above object may be attained by the following preferable embodiments.

(1) A radiation image reading system of the invention is characterized in that the radiation image reading system is equipped with an acceptance inputting means installed at the position to accept a patient and with plural radiation image reading apparatuses which is connected with the acceptance inputting means and reads a radiation image of the radiographed region of a patient, and registration information of a patient inputted from the acceptance inputting means is transmitted respectively to each radiation image reading apparatus, and then, when the transmitted registration information is canceled, information of the cancellation is transmitted to the radiation image reading apparatus which has received the registration information, and the canceled registration information is transmitted again to another radiation image reading apparatus.

In the invention, when reading of radiation images is canceled on a certain radiation image reading apparatus, information of the cancellation is transmitted to the image reading apparatus, and the canceled registration information is transmitted again to another radiation image reading apparatus. Therefore, it is possible to switch the apparatus for reading radiation images to another apparatus simply, and thereby to continue the reading of radiation images smoothly. Further, if the registration information is eliminated from the radiation image reading apparatus, it is possible to reduce confusion that plural reading apparatuses conduct reading based on the same registration information.

(2) In the radiation image reading system of (1), it is possible to arrange so that the cancellation information mentioned above and the canceled registration information stated above may be transmitted from the acceptance inputting means. Due to this, changes of radiation image reading apparatuses can be controlled in a centralized manner in the course of acceptance, and changes of apparatuses for reading radiation images can be made more smoothly.

(3) In the radiation image reading system of (1) or (2), by arranging so that the registration information may be canceled in each radiation image reading apparatus stated above, when the radiation image reading apparatus becomes unable to read radiation images for some reasons, for example, it is possible to cancel on the apparatus side, which is convenient in using apparatuses.

(4) In the radiation image reading system of (3), it is possible to arrange so that the acceptance inputting means is equipped with a display section, and the cancellation information is transmitted from the radiation image reading apparatus to the acceptance inputting means and is displayed on the display section, and the canceled registration information is transmitted from the acceptance inputting means to another radiation image reading apparatus.

(5) Another radiation image reading apparatus of the invention is characterized in that there are provided plural radiation image reading apparatuses each having a display section for displaying registration information of a patient and reading radiation images of a radiographed region of a patient, registration information of the plural radiation image reading apparatuses can be displayed on the display section of the radiation image reading apparatus, the registration information of the other radiation image reading apparatus can be canceled from one radiation image reading apparatus, and the canceled registration information can be transmitted to another radiation image reading apparatus from the radiation image reading apparatus on which the registration information has been canceled.

In the invention, when registration information of another radiation image reading apparatus is canceled from one radiation image reading apparatus by displaying the registration information of the other radiation image reading apparatus on the display section of each radiation image reading apparatus, it is possible to cancel the registration information on the apparatus side and to switch the apparatus for reading the radiation image to the other apparatus, because the canceled registration information can be transmitted to the other radiation image reading apparatus. In other words, it is possible to observe, on the display section of each radiation image reading apparatus, the information based on registration information relating to images which will be read by other reading apparatus. Therefore, when another apparatus is busy, it is possible to cancel registration information of the busy apparatus and to receive the registration information. If this is applied to the total radiation image reading systems so that registration information of the apparatuses of the total systems may be displayed, the total systems can conduct efficient reading.

(6) In the radiation image reading system of one of (1) to (5), it is also possible to arrange so that each radiation image reading apparatus mentioned above may read radiation images accumulated and recorded on a semiconductor X-ray detecting element.

(7) In the radiation image reading system of one of (1) to (6), when each radiation image reading apparatus mentioned above has a function as a radiation image radiographing apparatus which accumulates and records radiation images on a semiconductor X-ray detecting element, it is possible to make the aforesaid changes to other apparatuses smoothly and simply even in the case of radiographing radiation images, and to constitute a radiation image radiographing and reading system which is equipped with the aforesaid function.

(8) In the radiation image reading system of one of (1) to (7), it is also possible to arrange so that the registration information stated above may include identification information of a patient and at least one of radiographed regions of a patient, a radiographing method and a size of a recording medium used for radiographing. Due to this, each apparatus can obtain identification information of a patient and information of radiographing. Thus, based on the identification information, it is possible to identify image information in the course of reading radiation images. Due to this, it is possible to design to make an apparatus subjected to the change to be the optimum apparatus in accordance with the contents of registration information.

(9) In the radiation image reading system of one of (1) to (8), it is further possible to arrange so that a storage means which stores the registration information may further be provided. Due to this, it is possible to make registration information to be stored so that it may be transmitted from the storage means as occasion demands, or necessary registration information may be obtained through access of an acceptance inputting means or of each apparatus. With regard to the storage means, when those having relatively large storage capacity such as a server are provided on all systems, centralized control is possible and information control is simple, or a storage section such as a hard disk may also be provided dispersedly on an acceptance inputting means and on each apparatus.

(10) The radiation image reading method of the invention includes a step to input acceptance information in an acceptance inputting means installed at the position where a patient is accepted, a step to transmit the inputted registration information of a patient to each of plural radiation image reading apparatuses conducting reading of radiation images from the acceptance inputting means, a step to transmit, when transmitted registration information is canceled, the canceled information to the radiation image reading apparatus which has received the registration information, and a step to transmit again the canceled registration information to another radiation image reading apparatus. Due to this, it is possible to simply switch to another apparatus so that it may read radiation images to continue reading of radiation images smoothly.

(11) In the radiation image reading method of (10), by transmitting the canceled information and the canceled registration information from the acceptance inputting means, changes of radiation image reading apparatuses can be controlled in a centralized manner at a reception, and thereby, the changes can be made smoothly.

(12) In the radiation image reading method of (10), by canceling the registration information on each of the radiation image reading apparatuses, when the radiation image reading apparatus becomes unable to read radiation images for some reasons, for example, it is possible to cancel on the apparatus side, which is convenient for the use of apparatuses. In this case, the apparatus from which the registration information is canceled can transmit the canceled registration information to another apparatus.

BRIEF DESCRIPTION OF THE DRAWINGS

FIG. 2 is a diagram showing an example of a display section of an acceptance inputting apparatus shown in FIG. 1.

FIG. 3($a$) shows an example of a display section of a radiation image radiographing and reading apparatus shown in FIG. 1, and FIG. 3($b$) shows an example of a display section of another radiation image radiographing and reading apparatus shown in FIG. 1.

DETAILED DESCRIPTION OF THE PREFERRED EMBODIMENT

Embodiment of the Invention

Figure 1:
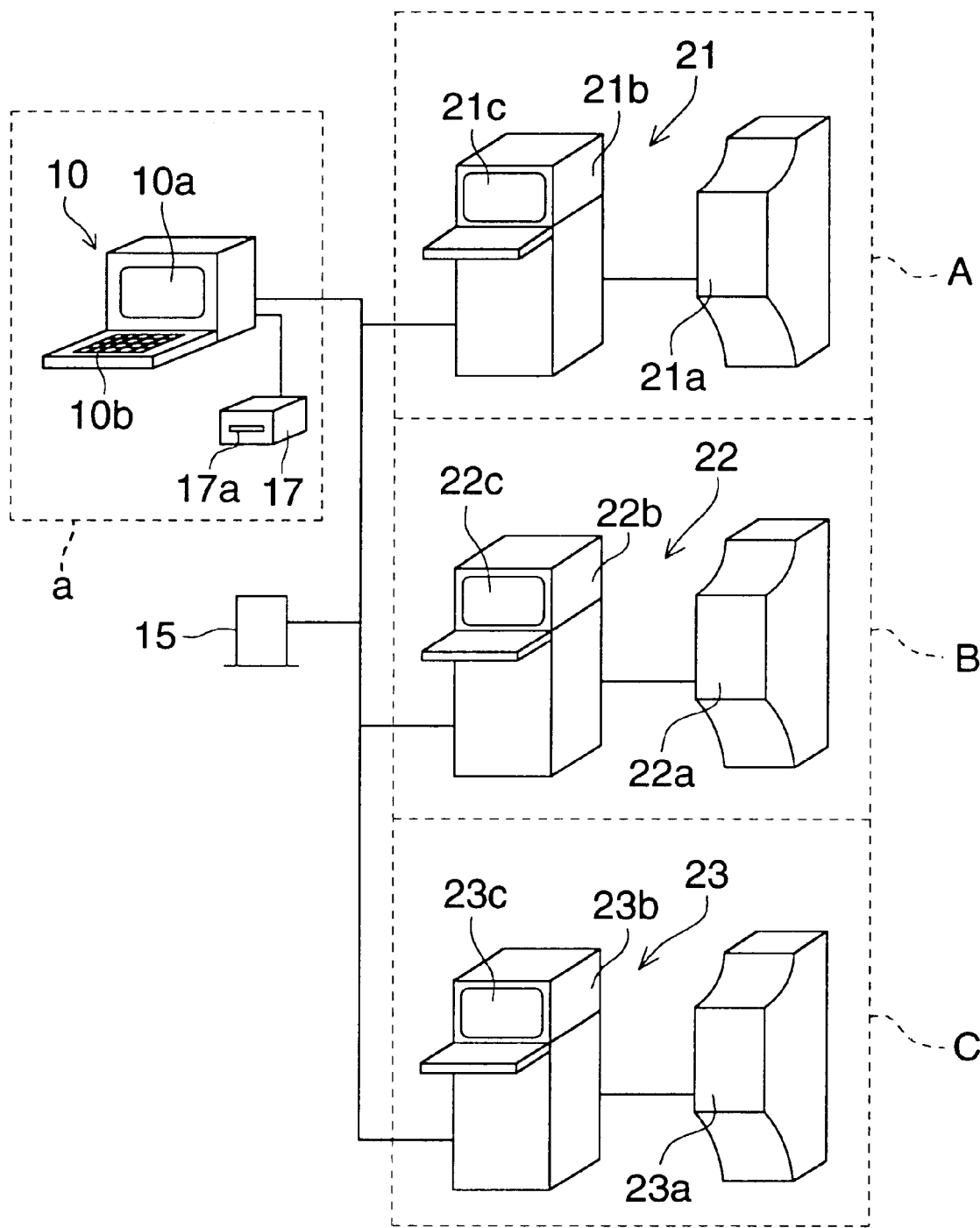
FIG. 1 is a diagram showing the structure of a radiation image radiographing and reading system in each embodiment of the invention.

The first embodiment through the third embodiment of the invention will be explained as follows, referring to drawings. FIG. 1 is a diagram showing the structure of a radiation image radiographing and reading system in each embodiment of the invention, FIG. 2 is a diagram showing an example of a display section of an acceptance inputting apparatus in FIG. 1, and FIG. 3 represents diagram (a) showing an example of a display section of a radiation image radiographing and reading apparatus in FIG. 1 and diagram (b) showing an example of a display section of another radiation image radiographing and reading apparatus in FIG. 1.

The structure of the radiation image radiographing and reading system in the present embodiment will be explained first, referring to FIG. 1. This radiation image radiographing and reading system is equipped with acceptance inputting apparatus 10 representing an acceptance inputting means installed in receptionist room a (shown with broken lines in FIG. 1) where reception work for the department of radiology in a hospital is done, first upright type radiation image radiographing and reading apparatus 21 which can radiograph while a patient is standing, and can read radiographed radiation images, the same second upright type radiation image radiographing and reading apparatus 22, the same third upright type radiation image radiographing and reading apparatus 23, and server 15 which is connected with apparatuses 10, 21, 22 and 23 and can store registration information of patients.

Each of radiation image radiographing and reading apparatuses 21–23 is equipped with each of radiographing sections 21$a$, 22$a$ and 23$a$ which can radiograph the chest while a patient is standing, each of controllers 21$b$, 22$b$ and 23$b$ which control radiographing and reading of radiation images, and with each of display sections 21$c$, 22$c$ and 23$c$ which display registration information of patients. Each of the radiation image radiographing and reading apparatuses 21, 22 and 23 is installed in each of radiographing and reading rooms A, B and C, as shown with broken lines in FIG. 1.

Acceptance inputting apparatus 10 in FIG. 1 is equipped with display section 10$a$ composed of CRT which can display prescribed information such as acceptance information, and with inputting section 10$b$ which can conduct key entry for prescribed information. Further, to the acceptance inputting apparatus 10, there is connected reader 17 where a recording card such as a patient identification card is inserted in reading opening 17$a$ so that acceptance information stored in the recording card may be read, and information thus read can be taken in the acceptance inputting apparatus 10.

Each of the radiation image radiographing and reading apparatuses 21–23 is constituted, in which a semiconductor X-ray detecting element which accumulates and records radiation images through irradiation of radiation is used, and radiation is irradiated on the semiconductor X-ray detecting element, and then, electric signals corresponding to an amount of radiation irradiated on the X-ray detecting element are generated, and by reading the electric signals, image information is read from the semiconductor X-ray detecting element, it is possible to record them on another recording medium. After reading this image information, the image information remaining on the semiconductor X-ray detecting element is erased to be ready for image recording and reading by the next irradiation of radiation.

First Embodiment

The first embodiment of the radiation image radiographing and reading system stated above will be explained. In this embodiment, patient registration information accepted by acceptance inputting apparatus 10 is displayed in succession on its display section 10$a$, and the registration information is sent to each of apparatuses 21–23 which are in charge of radiographing and reading for radiation images, through server 15, so that each of display sections 21$c$–23$c$ may display each patient taken care by each apparatus.

FIG. 2 shows an example of display section 10$a$ of the acceptance inputting apparatus 10. On the display section 10$a$, patient name 91, identification number (ID No.) 92, radiographed region 93, radiographing and reading room 94 and ID of a radiographing and reading apparatus of each patient are displayed for all patients accepted.

An example of display section 21$c$ of the first radiation image radiographing and reading apparatus 21 is shown in FIG. 3($a$), and an example of display section 22$c$ of the second radiation image radiographing and reading apparatus 22 is shown in FIG. 3($b$). Registration information such as patient name 91 for which the radiation image radiographing and reading are conducted in radiographing and reading room A where radiation image radiographing and reading apparatus 21 is installed is displayed on display section 21c as shown in FIG. 3(a), and registration information such as patient name 91 for which the radiation image radiographing and reading are conducted in radiographing and reading room B where radiation image radiographing and reading apparatus 22 is installed is displayed on display section 22c as shown in FIG. 3(b).

An arrangement is make so that when radiographing and reading of radiation images are not conducted in each of apparatuses 21–23 for some reasons, cancel information is sent to its radiation image radiographing and reading apparatus from acceptance inputting apparatus 10, then, registration information of a patient which has already been accepted is erased from the display section of the radiation image radiographing and reading apparatus, and the registration information of the patient thus erased is sent to another radiation image radiographing and reading apparatus.

Cancel means to cancel registration of a patient conducted to plan reading in each radiation image reading apparatus. Namely, it means to cancel the plan for each reading apparatus to read.

Operations of the radiation image radiographing and reading system stated above will be explained. After acceptance of a patient has been finished at acceptance room A, a receptionist inputs registration information brought by each patient, for example, a patient's chart into acceptance inputting apparatus 10 from inputting section 10b, based on acceptance information of the patient. Or, the receptionist can input registration information by inserting a patient ID recorded card into reading opening 17a of reader 17, and by reading the recorded information. In this case, the patient can insert ID recording card directly into the reading opening 17a of reader 17, skipping the receptionist. The registration information contains a patient identification information such as a name of a patient, the distinction of sex, a date of birth, and an identification (ID) number, radiographed regions, a radiographing method and a size of a semiconductor X-ray detecting element for radiographing.

Next, all pieces of registration information of all patients are displayed on display section 10a of acceptance inputting apparatus 10, as shown, for example, in FIG. 2, while, registration information of each patient is sent to server 15 from acceptance inputting apparatus 10, then, stored and registered. Then, registration information of each patient is sent to each of apparatuses 21–23 which are in charge of radiographing and reading of radiation images, and registration information of a patient taken care is displayed on a display section of each of apparatuses 21–23, as shown, for example, in FIGS. 3(a) and 3(b). In each of radiation image radiographing and reading apparatuses 21–23, radiographing and reading of radiation images are conducted in succession for patients displayed on each of display sections 21c–23c.

Referring, for example, to FIG. 3(a), in this case, when radiographing and reading of radiation images are required to be discontinued, before radiographing and reading of radiation images for patient " . . . Sato" for some reasons cancel information to cancel registration information of the patient " . . . Sato" is sent from acceptance inputting apparatus 10 to apparatus 21, and the registration information is erased from the display section 21c. Then, the registration information of the patient " . . . Sato" is sent by the acceptance inputting apparatus 10 to apparatus 22 to be displayed on display section 22c of the apparatus 22 as shown in FIG. 3(b). In this way, even when radiographing and reading can not be conducted on either one of plural radiation image radiographing and reading apparatuses for some reasons, radiographing and reading can be conducted on another apparatus. Therefore, it is possible to switch to another apparatus simply and thereby to continue radiographing and reading smoothly. Due to this, a receptionist who observed display means 10a of the acceptance inputting apparatus 10 can switch the reading apparatuses in accordance with the state of working of apparatuses 21–23. Further, those who judge to cancel before canceling may also be apparatuses 21–23. In that case, after the information for canceling is sent from each of apparatuses 21–23 to acceptance inputting apparatus 10, registration information for each of apparatuses 21–23 is canceled by the acceptance inputting apparatus 10. Due to this, it is possible to fit to circumstance of each apparatus.

After radiographing of radiation images, reading of image information from a semiconductor X-ray detecting element is conducted, and registration information of a patient is read simultaneously. After that, the registration information can be recorded on a recording medium such as a film on which the registration information is recorded. Due to this, it is possible to make the image information to correspond to the patient information, and thereby to identify the film after recording.

Incidentally, when an apparatus to conduct radiographing and reading is switched as stated above, display on display section 10a of acceptance inputting apparatus 10 may also be changed, and in the examples in FIGS. 2 and 3, for example, display of radiographing and reading room 94 for a patient " . . . Sato" may also be changed from "A" to "B". Further, registration information of the canceled patient may also be changed in terms of display method, by using reversal display, without erasing the registration information on the display section of the original apparatus.

Second Embodiment

The second embodiment in the radiation image radiographing and reading system shown in FIG. 1 will be explained. In this embodiment, registration information of a patient accepted once in each of radiation image radiographing and reading apparatuses 21–23 can be canceled by judgment on the apparatus side.

In explanation of operations, referring, for example, to FIG. 2, when radiographing and reading of radiation images can not be continued on and after the patient " . . . Sato" in radiation image radiographing and reading apparatuses 21 for some reasons, the registration information of the patient " . . . Sato" in FIG. 3(a), for example, is erased from display section 21c of the apparatus 21, and information of the canceling is sent to acceptance inputting apparatus 10. Then, the registration information of the canceled patient is sent from the acceptance inputting apparatus 10 to the other apparatus 22 to display on display section 22c of the apparatus 22 as shown in FIG. 3(b).

When either one of plural radiation image radiographing and reading apparatuses can not conduct radiographing and reading for some reasons as stated above, it is possible to judge inability of conducting on that apparatus, and to send registration information to another apparatus so that the apparatus can conduct radiographing and reading. Therefore, the change of this kind can be made simply, and radiographing and reading of radiation images can be continued smoothly. Thus, radiographing and reading of radiation images can be conducted in the same way as in the first embodiment, as far as other points are concerned.

Third Embodiment

The third embodiment in the radiation image radiographing and reading system shown in FIG. 1 will be explained. In this embodiment, registration information of a patient registered in server 15 in each of radiation image radiographing and reading apparatuses 21–23 is selected, and the selected registration information of the patient is displayed on each display section of each of apparatuses 21–23 so that the registration information of the patient accepted once may be canceled by judgment on the apparatus side, then, the canceled registration information of the patient is sent from that apparatus to another one.

In explanation of operations, referring, for example, to FIG. 2, when radiographing and reading of radiation images can not be continued on and after the patient " . . . Sato" in radiation image radiographing and reading apparatuses 21 for some reasons, the registration information of the patient " . . . Sato" in FIG. 3(a), for example, is erased from display section 21c of the apparatus 21, and the canceled registration information of the patient is sent from the apparatus 21 to apparatus 22 to display it on display section 22c of the apparatus 22 as shown in FIG. 3(b).

When either one of plural radiation image radiographing and reading apparatuses can not conduct radiographing and reading for some reasons as stated above, it is possible to judge inability of conducting on that apparatus, and to send registration information from that apparatus to another apparatus so that the apparatus can conduct radiographing and reading. Therefore, the change of this kind can be made simply, and radiographing and reading of radiation images can be continued smoothly. Thus, radiographing and reading of radiation images can be conducted in the same way as in the first embodiment, as far as other points are concerned.

Fourth Embodiment

The fourth embodiment in the radiation image radiographing system shown in FIG. 1 will be explained as follows. The present embodiment represents an example wherein at least one of plural radiation image radiographing and reading apparatuses 21–23 in the radiation image radiographing system cancels the registration information registered in other radiographing and reading apparatuses 21–23. Operations in the example will be explained next.

On each of display means 21c–23c of radiation image radiographing and reading apparatuses, registration information of patients which are subjected to radiographing and reading by radiation image radiographing and reading apparatuses 21–23 as well as registration information of patients which are subjected to radiographing and reading by other radiation image radiographing and reading apparatuses 21–23 are displayed.

In radiation image radiographing and reading apparatus 22, let it be assumed that the apparatus has finished radiographing and reading for all patients to be subjected to radiographing and reading, for example, namely that the apparatus has become capable of conducting radiographing and reading for patients which have been planned to be conducted by other apparatuses. In such a case, a radiologist of radiation image radiographing and reading apparatus 22 observes, on display means 22c, the registration information of patients to be radiographed and read by other apparatuses 22 and 23, and cancels desired registration information from the registration information of patients to be radiographed and read by other apparatuses 22 and 23, thus, the radiologist has the canceled registration information transmitted from the apparatus 22 or 23 from which the registration information has been canceled so that he or she can register the registration information as that for the patient to be radiographed and read newly by radiographing and reading apparatus 21.

By doing the foregoing, it is possible to conduct radiographing and reading for patients who have been supposed to be subjected to radiographing and reading by other apparatuses, after considering the state of working of each apparatus and the state of working of other apparatuses. Due to this, efficient radiographing and reading of the system can be realized with a simple structure.

Though all of the radiation image radiographing and reading apparatuses 21–23 are of an upright type in the embodiment stated above, the invention is not limited to this.

Which radiation image radiographing and reading apparatus to transmit the canceled registration information to can be determined in accordance with radiographing regions included in the registration information Due to this, efficient radiographing and reading can be attained, and it becomes possible to conduct radiographing and reading matching the characteristics of the radiation image radiographing and reading apparatus.

Equally, even in the case of canceling registration information of other apparatuses, radiographed regions included in registration information can determine which registration information should be canceled and which registration information should be transmitted. Due to this, efficient radiographing and reading can be attained, and it is possible to conduct radiographing and reading matching the characteristics of the radiation image radiographing and reading apparatus.

Though the invention has been explained as stated above, referring to each embodiment, the invention is not limited to these embodiments, and it is possible to change them variously within a scope of the technical concept of the invention. For example, it is also possible to read radiation images by the use of an image pick-up element such as CCD, in addition to reading radiation images with a photomultiplier through a laser scanning beam from a semiconductor X-ray detecting element. Further, a radiation image radiographing and reading apparatus may also be a radiation image reading apparatus which conducts only reading of radiation images, and in this case, the system is constituted as a radiation image reading system.

The invention makes it possible to provide a radiation image reading system and a radiation image reading method wherein plural radiation image reading apparatuses are installed, and even when each apparatus becomes unable to read radiation images of a patient accepted once, a change of reading to other apparatuses can easily be made smoothly.

What is claimed is:

1. A radiation image reading system, comprising:
   a plurality of reading apparatus to read a radiation image and to produce image data; and
   an information transmitting apparatus to transmit information regarding a patient to a first reading apparatus of the plurality of reading apparatus so that the first reading apparatus is assigned a job to read a radiation image of the patient;
   wherein when the information regarding the patient transmitted to the first reading apparatus by the information transmitting apparatus is canceled, the information regarding the patient is transmitted by the information transmitting apparatus to a second reading apparatus which is distinct from the first reading apparatus to which the information regarding the patient was previously transmitted, so that the first reading apparatus is released from the job to read the radiation image of the patient and the second reading apparatus is assigned the job to read the radiation image of the patient.

2. The radiation image reading system of claim 1, wherein when the first reading apparatus receives a canceling request to cancel the information regarding the patient, the first reading apparatus cancels the information regarding the patient.

3. The radiation image reading system of claim 2, wherein the information transmitting apparatus transmits the canceling request to the first reading apparatus and transmits the canceled information regarding the patient to the second reading apparatus.

4. The radiation image reading system of claim 1, wherein each of plurality of reading apparatus comprises canceling means for canceling the information regarding the patient transmitted by the information transmitting apparatus.

5. The radiation image reading system of claim 1, wherein at least one of the plurality of reading apparatus comprises canceling means for canceling the information regarding the patient transmitted by the information transmitting apparatus.

6. The radiation image reading system of claim 5, wherein:
the information transmitting apparatus comprises a display, and
when at least one of the plurality of reading apparatus cancel the information regarding the patient, the reading apparatus which cancels the information regarding the patient transmits the canceling request to the information transmitting apparatus, the display indicates the canceling request transmitted to the information transmitting apparatus, and the information transmitting apparatus transmits the information regarding the patient corresponding to the canceling request indicated on the display to the second reading apparatus which is distinct from the first reading apparatus to which the information regarding the patient was previously transmitted.

7. The radiation image reading system of claim 1, wherein the plurality of reading apparatus comprise reading means for reading a radiation image recorded by a semiconductor X-ray detecting element.

8. The radiation image reading system of claim 7, further comprising a radiation source to emit radiation,
wherein each of the plurality of reading apparatus reads the radiation image formed on the semiconductor X-ray detecting element which records radiation emitted from the radiation source through an object to be radiographed.

9. The radiation image reading system of claim 1, wherein the information regarding a patient includes identification information of the patient and at least one of a radiographed section of the patient, a radiographing method and a size of a recording medium used for the radiography.

10. The radiation image reading system of claim 1, further comprising a memory to store the information regarding the patient.

11. The radiation image reading system of claim 10, wherein the information transmitting apparatus transmits the information regarding the patient stored in the memory to at least one of the plurality of reading apparatus.

12. A radiation image reading system, comprising:
a plurality of reading apparatus to read a radiation image,
at least one of the plurality of reading apparatus comprising:
a display to indicate information regarding a patient, wherein the display indicates information regarding another patient whose image is expected to be read by an other reading apparatus; and
canceling means for canceling the information regarding the another patient whose image is expected to be read by the other reading apparatus,
wherein when the canceling means of the at least one of the plurality of reading apparatus cancels the information regarding the another patient whose image is expected to be read by the other reading apparatus, the canceled information regarding the another patient is transmitted from the other reading apparatus to the at least one of the plurality of reading apparatus so that the other reading apparatus is released from the job to read the radiation image of the another patient and the at least one of the plurality of reading apparatus is assigned the job to read the radiation image of the another patient in place of the other reading apparatus.

13. The radiation image reading system of claim 12, wherein each of the plurality of reading apparatus comprises the display and the canceling means.

14. The radiation image reading system of claim 12, wherein the at least one of the plurality of reading apparatus further comprises a controller to control transmission of canceled information of the patient to another reading apparatus when the information regarding the patient expected to be read by the at least one of the plurality of reading apparatus is canceled by the canceling means of the another reading apparatus.

15. The radiation image reading system of claim 14, wherein each of the plurality of reading apparatus comprises the controller.

16. The radiation image reading system of claim 12, wherein each of the plurality of reading apparatus comprise reading means for reading a radiation image recorded by a semiconductor X-ray detecting element.

17. The radiation image reading system of claim 16, further comprising a radiation source to emit radiation, wherein the reading means reads the radiation image formed on the semiconductor X-ray detecting element which records radiation emitted from the radiation source through an object to be radiographed.

18. The radiation image reading system of claim 12, wherein the information regarding the patient includes identification information of the patient and at least one of a radiographed section of the patient, a radiographing method and a size of a recording medium used for the radiography.

19. The radiation image reading system of claim 12, further comprising a memory to store the information regarding the patient.

20. The radiation image reading system of claim 19 further comprising information transmitting apparatus which transmits the information regarding the patient stored in the memory to the at least one of the plurality of reading apparatus.

21. A radiation image reading system, comprising:
a plurality of reading apparatus to read a radiation image,
at least one of the plurality of reading apparatus comprising:

a display to indicate information regarding a patient, wherein the display indicates information regarding a patient whose image is expected to be read by an other reading apparatus; and canceling means for canceling the information regarding the patient whose image is expected to be read by the at least one of the plurality of reading apparatus, wherein when the canceling means of the at least one of the plurality of reading apparatus cancels the information regarding the patient whose image is expected to be read by the at least one of the plurality of reading apparatus, the canceled information regarding the patient is transmitted to the other reading apparatus so that the at least one of the plurality of reading apparatus is released from the job to read the radiation image of the patient and the other reading apparatus is assigned the job to read the radiation image of the patient in place of the at least one of the plurality of reading apparatus.

22. The radiation image reading system of claim 21, wherein each of the plurality of reading apparatus comprises the display and the canceling means.

23. The radiation image reading system of claim 21, wherein the at least one of the plurality of reading apparatus further comprises a controller to control transmission of the canceled information of the patient to the other reading apparatus when the information regarding the patient expected to be read by the at least one of the plurality of reading apparatus is canceled by the canceling means thereof.

24. The radiation image reading system of claim 23, wherein each of the plurality of reading apparatus comprises the controller.

25. A radiation image reading system, comprising:
input means for inputting information regarding a patient;
a display to indicate the information regarding the patient input by the input means, the display indicating information regarding another patient input to an other reading apparatus to which a job to read a radiation image of the another patient is assigned;
canceling means for canceling the information regarding the another patient input to the other reading apparatus; and
receiving means for receiving the information regarding the another patient canceled by the canceling means from the other reading apparatus so that the other reading apparatus is released from the job to read the radiation image of the another patient and a reading apparatus is assigned the job to read the radiation image of the another patient in place of the other reading apparatus.

26. A radiation image reading system, comprising:
input means for inputting information regarding a patient;
a display to indicate the information regarding the patient input by the input means, the display indicating information regarding another patient input to an other reading apparatus; and
a controller which controls transmission of the information regarding the patient to the other reading apparatus when the information regarding the patient input by the input means is canceled by the other reading apparatus so that a job to read a radiation image of the patient is assigned to the other reading apparatus.

27. A method of reading a radiation image, comprising steps of:
inputting reception information by reception input means provided at a location to receive a patient, the reception information including information regarding the patient;
transmitting the information regarding the patient to at least a radiation image reading apparatus of a plurality of radiation image reading apparatus so that the job to read a radiation image of the patient is assigned to the radiation image reading apparatus;
canceling the information regarding the patient transmitted to the radiation image reading apparatus of the plurality of radiation image reading apparatus; and
transmitting the canceled information regarding the patient to another radiation image reading apparatus other than the radiation image reading apparatus to which the information regarding the patient was previously transmitted, so that the reading apparatus to which the information regarding the patient was previously transmitted is released from the job to read the radiation image of the patient and the another radiation image reading apparatus is assigned the job to read the radiation image of the patient in place of the reading apparatus to which the information regarding the patient was previously transmitted.

28. The method of reading a radiation image of claim 27, wherein the step of the canceling includes a step of transmitting a canceling request to cancel the information regarding the patient to the radiation image reading apparatus to which the information regarding the patient was previously transmitted.

29. The method of reading a radiation image of claim 28, wherein the canceling request is transmitted by the reception input means and the canceled information regarding the patient is transmitted to the another radiation image reading apparatus by the reception input means.

30. The method of reading a radiation image of claim 28, wherein the canceling step is conducted by one of the plurality of radiation image reading apparatus.

* * * * *